United States Patent [19]

Matlin et al.

[11] Patent Number: 5,558,877
[45] Date of Patent: Sep. 24, 1996

[54] METHOD AND DEVICE FOR TREATMENT OF CANCER

[75] Inventors: Stephen A. Matlin, Birmingham; Andrew T. Wilkins, Chippenham, both of England

[73] Assignee: Roussel Uclaf, France

[21] Appl. No.: 356,911

[22] Filed: Dec. 15, 1994

[30] Foreign Application Priority Data

Dec. 23, 1993 [GB] United Kingdom .................. 9326255

[51] Int. Cl.[6] .................. A61F 6/14; A61F 6/06
[52] U.S. Cl. .................. 424/432; 424/430; 514/967
[58] Field of Search .................. 424/430, 432; 514/967

[56] References Cited

U.S. PATENT DOCUMENTS 4,202,880  5/1980  Fildes et al. .................. 424/78
5,145,847  9/1992  Bohlmann et al. .................. 514/182

FOREIGN PATENT DOCUMENTS 1064629  3/1966  United Kingdom .

Primary Examiner—Carlos Azpuru
Attorney, Agent, or Firm—Bierman & Muserlian

[57] ABSTRACT

A medical device for insertion into a vaginal cavity comprising an elastomeric ring containing a compound selected from the group consisting of a compound of the formula

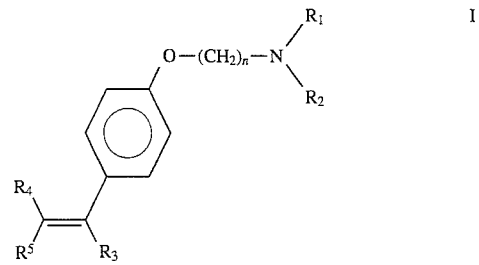

wherein $R_1$ is hydrogen or alkyl of 1 to 6 carbon atoms, $R_2$ and $R_5$ are individually alkyl of 1 to 6 carbon atoms, n is an integer from 2 to 6, $R_3$ and $R_4$ are individually aryl of 6 to 12 carbon atoms optionally substituted with 1 or 2 members of the group consisting of halogen and alkyl and alkoxy of 1 to 6 carbon atoms and their non-toxic, pharmaceutically acceptable acid addition salts for the treatment and prevention of cancer.

6 Claims, No Drawings

METHOD AND DEVICE FOR TREATMENT OF CANCER

STATE OF THE ART

Special medical devices adapted for placement or implantation into a living body are known and typically comprise a composite e.g. an elastomer ring which is inert in the environment of use and an active compound which is to be released from the inert matrix at a controlled rate for a prolonged period of time. This type of pharmaceutical preparation is to be contrasted with other types of pharmaceutical compositions which release the medication by dissolution in the gastro-intestinal tract as in an oral tablet, capsule or an aqueous solution.

It is well known that silicone polymers provide an inert carrier from which a pharmaceutically active compound can be released into a surrounding environment. For example, EP-A-050867 discloses pharmaceutical preparations containing a silicone elastomer and a pharmacologically active substance which may be implanted or inserted into a part of the body where it is desired for the pharmaceutically active substance to be released. WO-92-18101 discloses vaginal rings made of a silicone material and a pharmacologically active substance which are used for the treatment of bacterial vaginosis.

The medical devices described in the prior art can only be applied to very specific purposes as they have a problem in that the amount of the medicaments released from the silicone matrix is low and higher doses cannot be sustained for a prolonged period of time at a defined level. As a result, it is necessary to frequently replace these devices with "fresh" preparations containing a high loading of the drug to be administered. This results in unnecessary expense and discomfort to the user since these pharmaceutical preparations have to be frequently inserted and removed from the body part in which the medicament is to be released.

There has been a great deal of interest recently in the treatment of cancer, particularly breast cancer. Several methods of treatment have been developed in recent years and also the prophylaxis of breast cancer in high risk persons has been discussed. In British patent No. 1,064,629, a group of aromatic compounds has been disclosed, which are highly active substances for the treatment of cancer, but have some significant side effects when given orally.

OBJECTS OF THE INVENTION

It is an object of the invention to provide a novel medical device for the treatment of cancer and to provide a novel method of treating or preventing cancer in warm-blooded animals.

These and other objects and advantages of the invention will become obvious from the following detailed description.

THE INVENTION

The novel medical device of the invention for insertion into a vaginal cavity is comprised of an elastomeric ring containing a compound selected from the group consisting of a compound of the formula

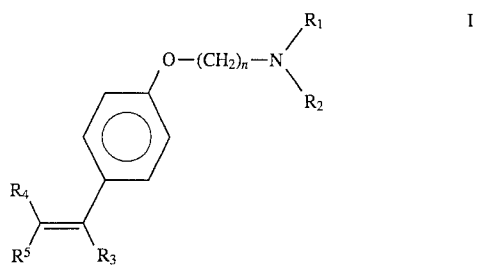

wherein $R_1$ is hydrogen or alkyl of 1 to 6 carbon atoms, $R_2$ and $R_5$ are individually alkyl of 1 to 6 carbon atoms, n is an integer from 2 to 6, $R_3$ and $R_4$ are individually aryl of 6 to 12 carbon atoms optionally substituted with 1 or 2 members of the group consisting of halogen and alkyl and alkoxy of 1 to 6 carbon atoms and their non-toxic, pharmaceutically acceptable acid addition salts.

The devices can advantageously be used for the prophylaxis and treatment of breast cancer of diverse origins and to treat pancreatic carcinoma, endometrial carcinoma, ovarian cancer and renal carcinoma.

As the pharmacologically active compound, a substance of formula Ia known as tamoxifen is preferably used:

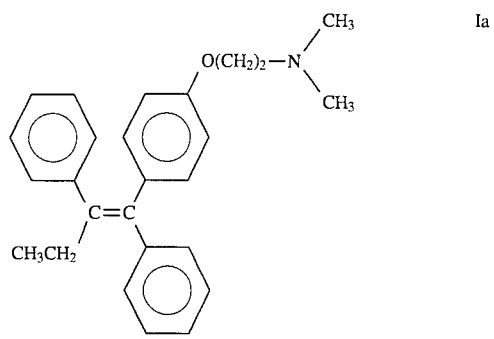

It is also possible to use a non-toxic, pharmaceutically acceptable acid addition salt of tamoxifen, e.g. the citrate of tamoxifen. The use of certain lipophilic salts can improve both the release from the device and absorption into the systemic circulation. Examples of such salts include the tamoxifen salts of pamoic acid ($C_{23}H_{16}O_6$) and stearic acid ($C_{18}H_{36}O_2$).

The elastomer ring of the invention consists preferably of a silicone elastomer, but other elastomers like polyethylene cellulose acetate or copolymers on the basis of ethylene and vinyl acetate can be used. The silicone elastomer used in the invention can be any medical grade elastomer which is suitable for use as a drug matrix for encapsulating a drug to be administered in a controlled release and which is inert in the environment of use.

Vaginal rings can also be made with a combination of silicone and thermoplastic elastomers, for example a device may have a core made from a suspension of drug in ethylene-vinyl acetate and a sheath made from silicone.

Particularly preferable silicone elastomers are those medical grades that consist of polydimethylsiloxane chains that contain silanol (—OH) functionalities. Incorporated into the elastomer formulation is a silicate ester cross linking agent e.g. n-propyl orthosilicate at a level of between 0.1 and 20 %, preferably between 1 and 5%, by weight.

The preferred elastomer contains either a diatomaceous earth filler or a fused silica filler at levels of between 5 to 60%, preferably 20 to 26%, by weight. Cross linking of the elastomer is facilitated by the use of tin (II) catalysts such as tin (II) 2-ethylhexanoic acid which is added to the elastomer in ratios of between 1 to 16 parts by weight of catalyst to 800 parts by weight of elastomer. Such presently available commercial elastomers are SILASTIC QCF 7 3099 (also designated X7-3099 and Q7-3099) and SILASTIC X7-4977 (Dow Corning Corporation, Valbonne, France).

Alternatively, a grade of silicone that includes vinyl (SiCH=CH$_2$) functionalities in the polydimethylsiloxane structure that cross link after treatment with a platinum catalyst may be used. Examples of such polymers are SILASTIC MDX4-4210, SILASTIC Q7-4735 and SILASTIC Q7-4750. In addition, silicones where the polydimethylsiloxane chains are cross linked after treatment with a free radical can be used e.g. a peroxide.

The pharmacologically active ingredients which can be used in the present invention are compounds of formula I, but preferably the compound of formula Ia. These compounds are readily available and can be prepared as disclosed in British patent No. 1,064,629.

The amount of the pharmacologically active compound loaded into the silicone elastomer is not limited and may be contained in the pharmaceutical preparation of the invention in amounts of 30 or more weight percent of the medical device with the loading level of the pharmacologically active ingredient being based solely on the compatibility of the ingredient of formula I with the silicone elastomer matrix. Preferably, the active compound is contained in the medical device of the invention in an amount of 1 to 30 percent, especially preferred is 10 to 25 percent, by weight based on the weight of the medical device.

Additives may be added to the polymer to help control drug release. The additives used in the invention should be compatible with the elastomer and compatible with the pharmacologically active compound of formula I to be contained in the elastomer. These include permeation enhancers e.g. coconut oil, Azone and vegetable oil, permeation inhibitors e.g. methyl cellulose and lactose, osmotic agents to imbibe water into the device e.g. salts such as sodium chloride, potassium chloride and sodium phosphate, pH adjusting agents e.g. disodium hydrogen orthophosphate, Na$_2$HPO$_4$ and viscosity modifiers e.g. a low molecular weight silicone fluid such as Dow Corning medical fluid 360. The said additives are to be incorporated into the device at levels of between 0 and 50%, preferably from 2 to 20%, by weight.

The medical device comprising the elastomer ring has an average outer dimension of 2 to 10 cm with the exact size depending on the particular application. Vaginal rings normally have an outer diameter of 4 to 8 cm, preferably from 5 to 7 cm and most preferred from 5 to 6 cm. The medical device normally has a minimum total weight of 0.9 g and a maximum total weight of 110 g. Preferred vaginal rings weigh from 5 to 16 g, and they can be used as a source of active compound for several months.

The width of the ring cross section normally is from 0.4 to 2.0 cm, preferably from 0.6 to 1.0 cm. The medical device of the invention can be made with different types of geometries. In practice, for intra-vaginal application, the core type ring and the shell type devices are especially preferred.

In a core type vaginal ring, the core is produced from a suspension of the active compound in the elastomer which forms the drug reservoir. The core is coated with one or more layers of polymeric material that preferably contain no active compound. This coating helps to control the rate of drug delivery. The core may run continuously through the ring or it may be a partial length or consist of several parts.

The medical device is preferably a multi-layer vaginal ring comprising a supporting ring free of the active compound, a second layer which is the drug reservoir and contains the active compound of formula I and as a third layer, a coating layer which covers the layer with the active substance. This type of device, called the shell type ring, is used where large diameter cores are preferred to maintain sufficient release of the active compound, and where an unnecessary wastage of active compound should be avoided.

In principle, it is also possible to use a matrix type of vaginal ring which is made from a homogenous suspension of active compound in the polymer. The matrix type ring releases the highest dose of active compound. A further type of vaginal ring consists of a central core containing the elastomer with no drug and a coating containing the active compound and the elastomer (suspension). The central core can also contain air only.

Different methods can be used for the preparation of the medical devices. According to a further aspect of the invention, there is provided a process for the preparation of a medical device comprising an elastomer ring containing a pharmacologically active compound of formula I as described above by using an injection molding or an extrusion processes.

Injection molding or extrusion technique may be used to prepare the elastomer rings. For the injection molding process, the fluid polymer is injected into a mold of the desired shape, e.g. a torus shape mold. The fluid polymer sets in the mold either by a cross linking reaction or by cooling of the melt (e.g. for ethylene-vinyl acetate) The general process may be modified to produce the other types of devices described above.

The extrusion process involves the pushing of a viscous polymeric material through a die to produce a continuous length of material known as an extrudate. Co-extrusion involves the simultaneous extrusion of two or more dissimilar materials that come together in a manifold to produce a multilayered structure. For the preparation of vaginal rings, the cylindrical extrudate has to be cut into lengths and the two ends joined. This can be done by placing in toroid molds which are heated to effect crosslinking.

The medical devices of the invention can also be made using a pultrusion technique where a central core is extruded separately and this single length of material is fed back into an extruder where an outer layer is extruded around it. Alternatively, a sheath of polymer could be injected around an extruded core.

According to a further aspect of the invention, there is provided a method of treatment or the prophylactic therapy of cancer in warm-blooded animals, including humans, which comprises inserting a medical device as hereinbefore described into the vagina of said subject. The preferred method of treatment or of prophylactic therapy is for breast cancer.

In the following examples, there are described several preferred embodiments to illustrate the invention. However, it should be understood that the invention is not intended to be limited to the specific embodiments.

EXAMPLE I

Preparation of a vaginal ring containing tamoxifen 512.89 g of the base polymer Silastic® 382 (less the catalyst) were prepared by mixing 500 g of Silastic® QCF 7 3099 with 12.89 g of propyl orthosilicate with a paddle mixer and the mixture was degassed under vacuum. The drug/polymer mixture was prepared by adding 1.0 g of tamoxifen powder directly to 3 g of the polymer base (less the catalyst) and mixing with a paddle mixer. The mixture was then degassed under vacuum.

Manufacture of the rings was effected by injection molding. The polymer base and drug polymer mixture were activated with the stannous octoate catalyst immediately before each injection. The molds were made from polymethylmethacrylate and the moldings were cured at 600° C. for 15 minutes. Two devices were produced. One was a core type ring that contained a 4.4 mm diameter core. The other was a shell type ring that contained an 8.3 mm diameter drug reservoir. The shell type design ring contained a 5.4 mm inert inner core. Both devices had external dimensions of 55 mm overall diameter and 9.5 mm cross sectional diameter. The cure could have been performed at a higher temperature for a shorter time, if metal molds had been used e.g. 2 minutes at 80° C. The 4.4 mm diameter core device contained 0.58 g of the active compound and the 8.3 mm diameter shell device contained 1.25 g of the active compound. The total weight of each ring was 11 g.

The vaginal route for tamoxifen delivery has several advantages over oral administration, namely: a) The continuous release avoids concentration peaks that occur following oral administration of the active compound. b) Improved patient compliance. This is particularly important when the compound is used for prophylaxis therapy where there is very little motivation for a "healthy" patient to remember to take tablets every day. c) A common side effect of the oral tablet containing a compound of formula I is gastrointestinal disturbance. A vaginal ring helps those patients who suffer tolerance problems with the oral tablets. d) Tamoxifen delivered through the vagina results in increased bioavailability over the oral route, which leads to a reduced risk of side effects.

EXAMPLE 2

The rate of tamoxifen release from the 4.4 mm diameter core device was determined in vitro by suspending the ring in 500 ml of elution medium contained in a sealed glass bottle. The bottle was maintained at body temperature (37° C.) in a water bath and stirring was provided by a PTFE coated bar magnet that was powered using a submersible stirring pad. The elution medium was prepared by adjusting a 0.1M solution of potassium dihydrogen orthophosphate ($KH_2PO_4$, AnalaR grade, BDH, Poole, UK) to a pH of 3 with orthophosphoric acid.

Samples of the elution medium were taken every 24 hours and analyzed to determine the amount of tamoxifen released. Immediately after sampling, the elution medium was replaced with fresh medium. This prevented an accumulation of drug in the medium that might otherwise slow down the rate of drug release from the device. This mimics the in vivo situation where a constant blood flow ensures efficient removal of the drug from the local environment of the device. The results are shown in the following Table for the release rate study of the 4.4 mm diameter core device.

| Day | Tamoxifen release rate (mg day$^{-1}$) |
| --- | --- |
| 2 | 11.7 |
| 5 | 9.9 |
| 10 | 9 |
| 15 | 8.4 |

EXAMPLE 3

Due to the fact that the 8.3 mm diameter shell type device was designed for high drug release, frequent replacement of the elution medium was necessary and this was achieved using a flow-through system. The ring was suspended in elution medium in a bottle as described in Example 2. In addition, two tubes were sealed through the cap. One tube acted as an inlet to allow medium into the bottle and the other as an outlet to allow medium to leave the bottle and run to an effluent collection vessel. Flow of medium was induced with a peristaltic pump. Every 24 hours, the medium in the bottle was emptied into the effluent collection vessel and this was replaced with fresh medium. The volume of the effluent was determined and the effluent sampled and analyzed to determine the amount of tamoxifen released. The flow of medium was between 2 and 3 liters per 24 hours. The results of the release rate study of the 8.3 mm diameter shell device are in the following Table.

| Day | Tamoxifen release rate (mg day$^{-1}$) |
| --- | --- |
| 1 | 62.5 |
| 3 | 41.8 |
| 10 | 26.4 |
| 15 | 22.4 |
| 20 | 19.5 |
| 28 | 16.7 |

The in vitro release testing methods used in Examples 2 and 3 have been shown to give good in vivo correlation when used to test progesterone releasing contraceptive vaginal rings (see Matlin, et al., Progesterone-releasing vaginal rings for use in postpartum contraception. I. In vitro release rates of progesterone from core-loaded rings, Contraception, (1992), Vol. 45, pp. 329–341; and Landgren et al., Progesterone-releasing vaginal rings for use in postpartum contraception. II. Pharmacokinetic profiles in women. Contraception, (1992), Vol. 45, pp. 343–349).

EXAMPLE 4

Corresponding vaginal rings were prepared by using tamoxifen salts such as the citrate or other compounds of formula I.

Various modifications of the device and the method of the invention may be made without departing from the spirit or scope thereof and it is to be understood that the invention is intended to be limited only as defined in the appended claims.

What we claim is:

1. A medical device for insertion into a vaginal cavity consisting essentially of a silicone elastomeric ring containing 1 to 30% by weight of a compound of the formula

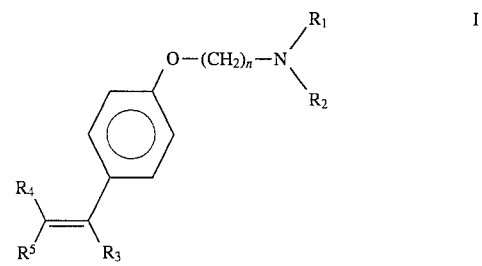

wherein $R_1$ is hydrogen or alkyl of 1 to 6 carbon atoms, $R_2$ and $R_5$ are individually alkyl of 1 to 6 carbon atoms, n is an integer from 2 to 6, $R_3$ and $R_4$ are individually aryl of 6 to 12 carbon atoms optionally substituted with 1 or 2 members of the group consisting of halogen and alkyl and alkoxy of 1 to 6 carbon atoms or its non-toxic, pharmaceutically acceptable acid addition salts.

2. A medical device of claim 1 wherein the compound has the formula

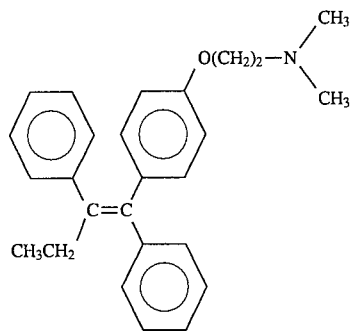

or fits non-toxic, pharmaceutically acceptable salt.

3. A medical device of claim 1 consisting essentially of 10 to 25% by weight of the compound of formula I based on the total weight of the device.

4. A medical device of claim 1 wherein the elastomer ring is a shell or core type ring of a silicone elastomer consisting essentially of 10 to 25% by weight of the device of a compound of formula I.

5. A method of treating breast cancer in female warm-blooded animals in need thereof comprising inserting into the vagina of said animals a medical device of claim 1 to release a therapeutically effective amount of Formula I or its non-toxic, pharmaceutically acceptable acid addition salts.

6. The method of claim 5 wherein the active "compound has the formula

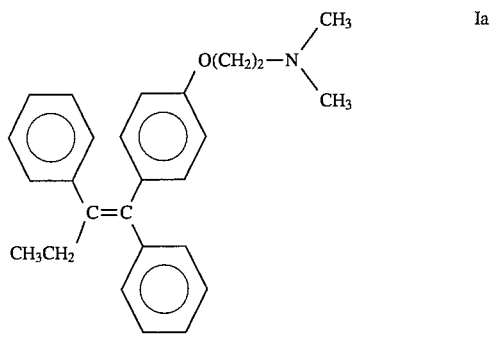

or a non-toxic, pharmaceutically acceptable salt thereof.

* * * * *